United States Patent
Aerykssen et al.

(10) Patent No.: US 9,029,489 B2
(45) Date of Patent: May 12, 2015

(54) POLYURETHANE (METH) ACRYLATES USING MODIFIED HYDROXYTHIOLS

(75) Inventors: James H. Aerykssen, Torrington, CT (US); Ahmet Nebioglu, Winsted, CT (US); Richard D. Zopf, Torrington, CT (US); Igor V. Khudyakov, Hickory, NC (US)

(73) Assignee: Dymax Oligomers and Coatings LLC, Torrington, CT (US)

( * ) Notice: Subject to any disclaimer, the term of this patent is extended or adjusted under 35 U.S.C. 154(b) by 605 days.

(21) Appl. No.: 12/825,273

(22) Filed: Jun. 28, 2010

(65) Prior Publication Data

US 2011/0319580 A1 Dec. 29, 2011

(51) Int. Cl.
| | |
|---|---|
| C08F 299/06 | (2006.01) |
| C07C 323/52 | (2006.01) |
| C08G 18/67 | (2006.01) |
| C08G 18/81 | (2006.01) |
| C09J 175/16 | (2006.01) |
| C08G 18/75 | (2006.01) |
| C08G 18/38 | (2006.01) |

(52) U.S. Cl.
CPC ............ C07C 323/52 (2013.01); C08G 18/755 (2013.01); C08G 18/3863 (2013.01); C08F 299/06 (2013.01); C08G 18/3855 (2013.01); C08F 299/065 (2013.01); C08G 18/3868 (2013.01); C08G 18/673 (2013.01); C08G 18/758 (2013.01); C08G 18/8175 (2013.01); C09J 175/16 (2013.01)

(58) Field of Classification Search
USPC ................. 526/309, 312, 333; 528/65, 373
See application file for complete search history.

(56) References Cited

U.S. PATENT DOCUMENTS

| | | | |
|---|---|---|---|
| 3,065,211 A | 11/1962 | Miford et al. | 526/211 |
| 4,094,843 A | 6/1978 | McGinniss | 524/560 |
| 4,108,840 A | 8/1978 | Friedlander | 525/412 |
| 6,596,786 B2 | 7/2003 | Purvis et al. | 522/35 |
| 6,998,011 B2 | 2/2006 | Schoenfeld et al. | 156/331.4 |
| 2010/0056722 A1 | 3/2010 | Thomas et al. | 525/123 |
| 2010/0075255 A1* | 3/2010 | Taguchi | 430/284.1 |

* cited by examiner

*Primary Examiner* — Richard A Huhn
(74) *Attorney, Agent, or Firm* — Roberts & Roberts, LLP

(57) ABSTRACT

The invention provides intermediates of the formula:

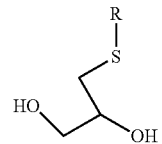

as well as a method of their preparation by reacting a thiol having at least two hydroxyl groups with a mono-unsaturated organic compound in the presence of a base catalyst. A polymerizable urethane acrylate oligomer or urethane methacrylate oligomer is formed by reacting a polyisocyanate with the intermediate. The polymerizable urethane acrylate oligomer or urethane methacrylate is blended with a polymerization initiator to form a composition which is useful in such applications as adhesives.

5 Claims, No Drawings

POLYURETHANE (METH) ACRYLATES USING MODIFIED HYDROXYTHIOLS

BACKGROUND OF THE INVENTION

1. Field of the Invention

The invention pertains to intermediates of the formula:

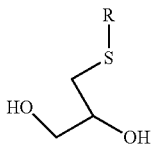

as well as a method of their preparation by reacting a thiol having at least two hydroxyl groups with a mono-unsaturated organic compound in the presence of a base catalyst. A polymerizable urethane acrylate oligomer or urethane methacrylate oligomer is formed by reacting a polyisocyanate with the intermediate. The polymerizable urethane acrylate oligomer or urethane methacrylate is blended with a polymerization initiator to form a composition which is useful in such applications as adhesives.

2. Description of the Related Art

Curable adhesive compositions are well-known in the art. In the past, many adhesives particularly anaerobic adhesives, have been rendered resistant to degradation at elevated temperatures by the inclusion of certain additives. For instance, U.S. Pat. No. 3,988,299 teaches a heat curable composition having improved thermal properties, which includes certain acrylate monomers and maleimide compounds.

While the addition to curable adhesive compositions of such compounds to render them resistant to thermal degradation provides reaction products with acceptable performance, it would be desirable to find alternative compounds to include in such formulations. Thus, there is an on-going search for additives to improve the thermal performance of reaction products of curable adhesives. In addition, it would be desirable from a commercial, economic, environmental, supply and regulatory standpoint to provide alternatives and/or replacements for maleimide-type materials for improving the resistance to thermal degradation of reaction products of radical-curable adhesive compositions.

It has been unexpectedly found that improved adhesive formulations can be prepared by preparing intermediates by reacting a thiol having at least two hydroxyl groups with a mono-unsaturated organic compound in the presence of a base catalyst. When this intermediate is reacted with a polyisocyanate reactive acrylate or methacrylate a polymerizable urethane acrylate oligomer or urethane methacrylate oligomer is formed. When blended with a polymerization initiator a curable adhesive is formed. When applied to a substrate or carrier and cured by heating or actinic radiation, the adhesive results in a product having improved impact toughness and/or impact resistance useful in a wide variety of applications.

A composition of the invention includes polyurethane (meth)acrylate oligomers (prepolymers), and formulations thereof, which contain residues of modified hydroxythiols in the oligomeric chain. Within the context of this invention, the term (meth)acrylate means either an acrylate or a methacrylate. These polyurethane (meth)acrylate oligomers will have a wide range of properties beneficial to industrial adhesive and coating applications due to the presence of both thioether functionality, which improve chemical and thermal resistance, and other functionalities that are incorporated through the hydroxythiol modification. Examples of such functionalities are carboxylic acids or other highly hydrophilic groups for water reduction/dilution, anti-fog coatings, and adhesion; hydrophobic groups for water resistance, adhesion to plastics and high refractive index groups for optical applications; silicone bearing groups for decreased surface tension, improved impact resistance, and anti-graffiti coatings; and (meth)acrylate groups for increased crosslink density, strength, and hardness. Other functionalities added to the oligomers change their pigment dispersion characteristics and therefore make them useful in inks. The ability to add pendant functionalities without compromising the physical properties such as tensile strength, scratch and chemical resistance, is especially important for commercial applications. For example in antifog coatings, having a high scratch and solvent resistance while keeping the antifog properties are contradictory and challenging. Prior techniques require expansive nanoparticles to obtain the necessary properties. With the present method it is possible to obtain scratch and solvent resistant coatings with very good antifog properties.

The preparation of the inventive oligomers is by a two stage process with the first stage being the modification of the hydroxythiol with the desired functionality. This is carried out through Michael Addition reaction of the hydroxythiol with a composition containing both the functionality and units of unsaturation, particularly acrylate. The product will be a (poly)ol with the number of thioether and functional groups equal to the starting number of thiol groups. This product, alone or with other polyols, is then reacted by standard methods with polyisocyanates and hydroxy (meth)acrylates or with monoisocyanate-(meth)acrylates to produce the polyurethane (meth)acrylate oligomer bearing the thioether and desired functionality.

SUMMARY OF THE INVENTION

The invention provides an intermediate of the formula

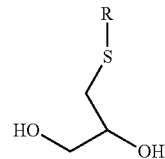

wherein R is a linear or branched $C_1$ to $C_{30}$ alkyl group, a linear or branched $C_3$ to $C_{30}$ alkenyl group, a $C_6$ to $C_{22}$ aryl group, a polyethylene glycol containing group, a (poly)ethylene glycol mono methyl ether containing group, a (poly)ethylene glycol mono ethyl ether containing group, a lauryl group, a silicone containing group, an alkoxysilane containing group, $Si(OCH_3)_3$ containing group, a fluorinated alkyl group, a brominated alkyl group, or a benzene derivative.

The invention also provides a method for forming an intermediate of the formula

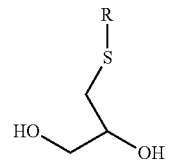

wherein R is a linear or branched $C_1$ to $C_{30}$ alkyl group, a linear or branched $C_3$ to $C_{30}$ alkenyl group, a $C_6$ to $C_{22}$ aryl group, a polyethylene glycol containing group, a (poly)ethylene glycol mono methyl ether containing group, a (poly)ethylene glycol mono ethyl ether containing group, a lauryl group, a silicone containing group, alkoxysilane containing group, $Si(OCH_3)_3$ containing group, a fluorinated alkyl group, a brominated alkyl group, or a benzene derivative, which comprises reacting a thiol having at least two hydroxyl groups with a mono-unsaturated organic compound in the presence of a base catalyst.

The invention further provides a method of forming a urethane acrylate or urethane methacrylate oligomer which comprises reacting a polyisocyanate with an intermediate of the formula

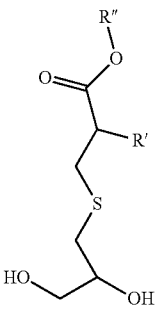

wherein
R'=—H, —CH$_3$;
R" is a linear or branched C$_1$ to C$_{30}$ alkyl group, a linear or branched C$_3$ to C$_{30}$ alkenyl group, a C$_6$ to C$_{22}$ aryl group, a polyethylene glycol containing group, a (poly)ethylene glycol mono methyl ether containing group, a (poly)ethylene glycol mono ethyl ether containing group, a lauryl group, a silicone containing group, an alkoxysilane containing group, Si(OCH$_3$)$_3$ containing group, a fluorinated alkyl group, a brominated alkyl group, or a benzene derivative.

The invention still further provides a polymerizable urethane acrylate oligomer or urethane methacrylate oligomer having one of the formulae (I), (II) or (III):

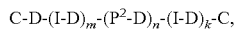

wherein:
C is a capping agent which is a monoalcohol acrylate having from 1 to 5 acrylate functionalities or a monoalcohol methacrylate having from 1 to 5 methacrylate functionalities;
D is a diisocyanate,
P$^2$ is a diol,
n is from 0 to 10;
m is from 1 to 5;
k is from 0 to 5;
I is an intermediate having the structure:

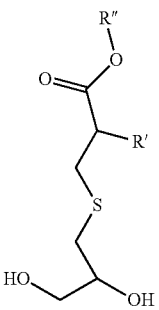

wherein
R'=—H, —CH$_3$;
R" is a linear or branched C$_1$ to C$_{30}$ alkyl group, a linear or branched C$_3$ to C$_{30}$ alkenyl group, a C$_6$ to C$_{22}$ aryl group, a polyethylene glycol containing group, a (poly)ethylene glycol mono methyl ether containing group, a (poly)ethylene glycol mono ethyl ether containing group, a lauryl group, a silicone containing group, an alkoxysilane containing group, Si(OCH$_3$)$_3$ containing group, a fluorinated alkyl group, a brominated alkyl group, or a benzene derivative;

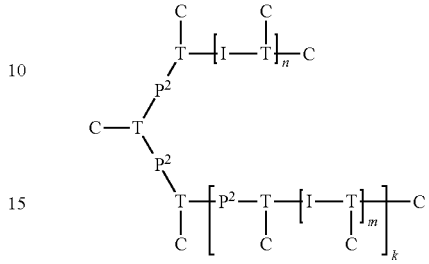

T is a triisocyanate;
n is from 1 to 10;
m is from 0 to 5;
k is from 1 to 10;

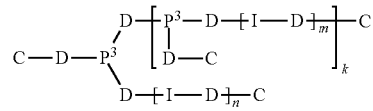

wherein P$^3$ is a triol;
n is from 0 to 10;
m is from 1 to 5;
k is from 1 to 10.

The above polymerizable urethane acrylate oligomer or urethane methacrylate oligomer may further comprise a polymerization initiator.

DESCRIPTION OF THE INVENTION

In embodiment of the invention pertains to an intermediate compound of the formula

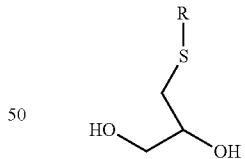

wherein R is a linear or branched C$_1$ to C$_{30}$ alkyl group, a linear or branched C$_3$ to C$_{30}$ alkenyl group, a C$_6$ to C$_{22}$ aryl group, a polyethylene glycol containing group, a (poly)ethylene glycol mono methyl ether containing group, a (poly) ethylene glycol mono ethyl ether containing group, a lauryl group, a silicone containing group, an alkoxysilane containing group, Si(OCH$_3$)$_3$ containing group, a fluorinated alkyl group, a brominated alkyl group, or a benzene derivative.

This intermediate compound may be prepared by reacting a thiol having at least two hydroxyl groups with a mono-unsaturated organic compound in the presence of a base catalyst. Examples of a thiol having at least two hydroxyl groups non-exclusively include at least one of 1-thioglycerol, 1-thiobutane-2,3-diol, 2-thio-1,4-butanediol, 2,2-bis(3-hydroxypropanoyloxymethy)butyl-3-sulfanylpropnoate, and 4-thio-1,16-hexanediol, 1-thiohexadecane-5,8-diol.

Non-exclusive examples of the mono-unsaturated organic compound comprises at least one of a monoacrylate, a mono (meth)acrylate, a mono allyl ether, a mono vinyl ether, maleic anhydride, a maleic anhydride ester and a maleic anhydride imide. More particularly, non-exclusive examples of the mono-unsaturated organic compound comprises at least one of a methyl (meth)acrylate, ethyl (meth)acrylate, propyl (meth)acrylate, butyl (meth)acrylate, pentyl (meth)acrylate, hexyl (meth)acrylate, isodecyl (meth)acrylate, lauryl (meth)acrylate, isobornyl (meth)acrylate, tetrahydrofurfuryl (meth)acrylate, ethylene glycol phenyl ether acrylate, phenylthioethyl acrylate, ethylene glycol methyl ether (meth)acrylate, diethylene glycol methyl ether (meth)acrylate, poly(ethyleneglycol) methyl ether (meth)acrylate, poly(propyleneglycol) methyl ether (meth)acrylate, silicone acrylate, 3-(trimethoxysilyl)propyl (meth)acrylate, 3-(triethoxysilyl)propyl (meth)acrylate, 3-(trimethoxysilyl)ethyl (meth)acrylate, trifluoroethyl acrylate, tetrafluoropropyl acrylate, pentafluoropropyl acrylate, heptafluorobutyl acrylate, dodecafluoroheptyl acrylate, pentabromophenyl acrylate, allyl butyl ether, allyl propyl ether, allyl ethyl ether, allyl methyl ether, allyl tetrafluoroethyl ether, allyl 1,1,2,3,3,3-hexafluoropropyl ether, allyl 2,4,6-tribromophenyl ether, cyclohexyl vinyl ether, dodecyl vinyl ether, ethylene glycol butyl vinyl ether, isobutyl vinyl ether, methyl vinyl ether, or propyl vinyl ether.

Useful examples of the base catalyst non-exclusively include diethyl ethanol amine, tri-n-butylamine, triethyl amine, 1,4-diazobicyclo[2.2.2]octane, triethanol amine, triisopropanol amine, dimethyl phenyl phosphine, and trioctyl phosphine.

An example of this method comprises reacting 1-thioglycerol of the formula

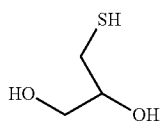

with a mono-acrylate or mono-methacrylate of the formula:

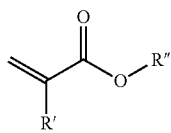

wherein R'=—H, —CH₃;
R" is linear or branched $C_1$ to $C_{30}$ alkyl group, a linear or branched $C_3$ to $C_{30}$ alkenyl group, a $C_6$ to $C_{22}$ aryl group, a polyethylene glycol containing group, a (poly)ethylene glycol mono methyl ether containing group, a (poly)ethylene glycol mono ethyl ether containing group, a lauryl group, a silicone containing group, an alkoxysilane containing group, $Si(OCH_3)_3$ containing group, a fluorinated alkyl group, a brominated alkyl group, or a benzene derivative, to thereby form an intermediate of the formula:

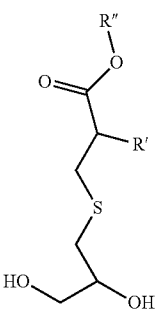

The reaction may be conducted under the following general conditions:

Reagents such as 1-thioglycerol and mono (meth)acrylate, are blended in the molar ratio of thioglycerol:mono (meth)acrylate of 1 to about 3, or, preferably 1 to about 2, or more preferably 1 to about 1. When (meth)acrylate is taken in a ratio more than 1:1, the excess of non-reacted (meth)acrylate present in the intermediate serves as a reactive diluent. A reaction vessel with 1-thioglycerol and mono (meth)acrylate is themostatted at a temperature of from about 20° C. to about 100° C., or preferably from about 30° C. to about 80° C., or more preferably from about 55° C. to about 65° C. A catalyst is added in a concentration of from about 600 to about 1800 ppm, or, preferably from about 800 to about 1400 ppm, or more preferably from about 800 to about 1200 ppm. Useful examples of the base catalyst non-exclusively include diethyl ethanol amine, tri-n-butylamine, triethyl amine, 1,4-diazobicyclo[2.2.2]octane, triethanol amine, triisopropanol amine, dimethyl phenyl phosphine, and trioctyl phosphine. Typical reaction time at 65° C. with a concentration of catalyst of from about 800 to about 1200 ppm is from about 2 to about 3 hours. An increase (decrease) of the temperature leads to acceleration (deceleration) of a reaction of the intermediate (I) formation.

Another embodiment of the invention is a method of forming a urethane oligomer (prepolymer) which comprises reacting a polyisocyanate with an intermediate of the formula

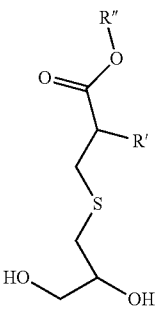

wherein
R'=—H, —CH₃;
R" is a linear or branched $C_1$ to $C_{30}$ alkyl group, a linear or branched $C_3$ to $C_{30}$ alkenyl group, a $C_6$ to $C_{22}$ aryl group, a polyethylene glycol containing group, a (poly)ethylene glycol mono methyl ether containing group, a (poly)ethylene glycol mono ethyl ether containing group, a lauryl group, a silicone containing group, an alkoxysilane containing group, Si(OCH$_3$)$_3$ containing group, a fluorinated alkyl group, a brominated alkyl group, or a benzene derivative. The polyisocyanate is preferably a diisocyanate, but may be a triisocyanate. Reagents, intermediate (I) with a structure presented above, is blended with polyisocyanate in the equivalent ratio of OH-groups of I:NCO-groups of polyisocyanate of 1 to about 10, or, preferably 1 to about 5, or more preferably 1 to about 3. Polyisocyanate is taken in the equivalent ratio of more than 1:1, non-reacted NCO groups present as chemically bound to I or as free isocyanate. Non-reacted NCO groups can participate in further urethane formation reactions. Reaction vessel with I and polyisocyanate is themostatted at a temperature of from about 20° C. to about 100° C., or, preferably from about 30° C. to about 80° C., or more preferably from about 60° C. to about 70° C. A catalyst should be added in the concentrations of from about 10 to about 1000 ppm, or, preferably from about 20 to about 700 ppm, or more preferably from about 50 to about 100 ppm. Useful examples of the urethane links formation catalysts non-exclusively include dibutyltin dilaurate (DBTDL), stannous octoate, diazobicyclo[2.2.2]octane, bismuth catalysts of urethane formation. Typical reaction time at 65° C. with a concentration of catalyst 100 ppm was from about 3 to about 4 hours. An increase (decrease) of the temperature leads to acceleration (deceleration) of a reaction of the intermediate formation.

Another embodiment of the invention is a polymerizable urethane acrylate oligomer or urethane methacrylate oligomer having one of the formulae (I), (II) or (III):

$$C\text{-}D\text{-}(I\text{-}D)_m\text{-}(P^2\text{-}D)_n\text{-}(I\text{-}D)_k\text{-}C, \quad (I)$$

wherein:
C is a capping agent which is a monoalcohol acrylate having from 1 to 5 acrylate functionalities or a monoalcohol methacrylate having from 1 to 5 methacrylate functionalities;
D is a diisocyanate,
P$^2$ is a diol,
n is from 0 to about 10; preferably from 0 to about 6, and more preferably from 0 to about 3,
m is from 1 to about 5; preferably from 1 to about 2, more preferably 1 to about 2,
k is from 0 to 5; preferably from 0 to about 3, more preferably from 0 to about 1
I is an intermediate having the structure:

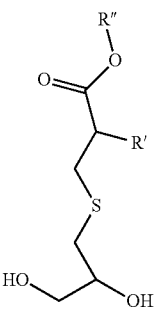

wherein
R'=—H, —CH$_3$;
R" is a linear or branched C$_1$ to C$_{30}$ alkyl group, a linear or branched C$_3$ to C$_{30}$ alkenyl group, a C$_6$ to C$_{22}$ aryl group, a polyethylene glycol containing group, a (poly)ethylene glycol mono methyl ether containing group, a (poly)ethylene glycol mono ethyl ether containing group, a lauryl group, a silicone containing group, an alkoxysilane containing group, Si(OCH$_3$)$_3$ containing group, a fluorinated alkyl group, a brominated alkyl group, or a benzene derivative;

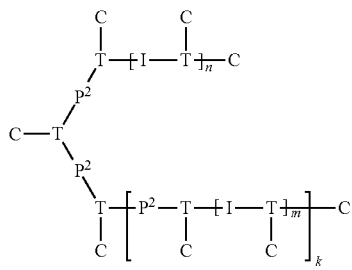

(II)

T is a triisocyanate;
n is from 1 to about 10; preferably from 1 to about 6, and more preferably from 1 to about 2,
m is from 0 to about 5; preferably from 0 to about 3, and more preferably from 0 to 1;
k is from 1 to 10; preferably from 1 to about 6, and more preferably from 1 to about 2;

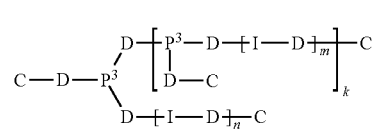

(III)

wherein P$^3$ is a triol;
n is from 0 to about 10; preferably from 0 to about 6, more preferably from 0 to about 3,
m is from 1 to about 5; preferably from 1 to about 3, more preferably from 1 to about 2,
k is from 1 to about 10, preferably from 1 to about 6, more preferably from 1 to about 2.

In a preferred embodiment, the polymerizable composition comprises a urethane acrylate oligomer or urethane methacrylate oligomer of the formula:

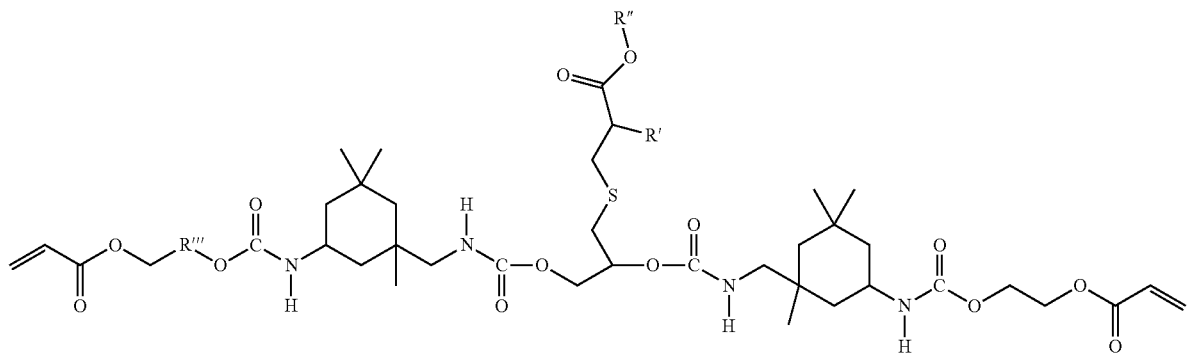

wherein n is 1 to 50,

R'=—H, —CH$_3$;

R"=is a linear or branched C$_1$ to C$_{30}$ alkyl group, a linear or branched C$_3$ to C$_{30}$ alkenyl group, a C$_6$ to C$_{22}$ aryl group, a polyethylene glycol containing group, a (poly)ethylene glycol mono methyl ether containing group, a (poly)ethylene glycol mono ethyl ether containing group, a lauryl group, a silicone containing group, an alkoxysilane containing group, Si(OCH$_3$)$_3$ containing group, a fluorinated alkyl group, a brominated alkyl group, or a benzene derivative,

R''' =

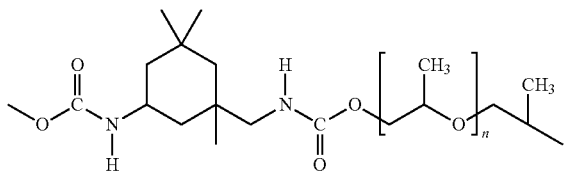

This reaction is a typical reaction of urethane (meth)acrylate formation with a suggested intermediate I as given about, or an intermediate with —NCO excess described above. A suggested reaction of urethane (meth)acrylate formation is as follows. Reagents, polyol of OH-functionality 2 or 3, is blended with an excess of polyisocyanate of NCO-functionality 2 or 3 in the equivalent ratio of OH-groups of polyols: NCO-groups of polyisocyanate as 1 to about 7, or preferably 1 to about 5, or more preferably 1 to about 4. A reaction vessel with polyol and polyisocyanate is themostatted at a temperature of from about 20° C. to about 100° C., or, preferably from about 30° C. to about 80° C., or more preferably from about 60° C. to about 70° C. A catalyst should be added in the concentrations of from about 10 to about 1000 ppm, or, preferably from about 20 to about 700 ppm, or more preferably from about 50 to about 100 ppm. Useful examples of the urethane links formation catalysts non-exclusively include dibutyltin dilaurate (DBTDL), stannous octoate, diazobicyclo[2.2.2]octane, bismuth catalysts of urethane formation. Typical reaction time at 65° C. with a concentration of catalyst 100 ppm is from about 3 to about 4 hours. An increase (decrease) of the temperature leads to acceleration (deceleration) of a reaction of urethane prepolymer formation. Upon completion of a reaction indicated by termination of disappearance of NCO characteristic absorption in the IR spectrum, an intermediate I is added to the mixture which has non-reacted NCO. It is a stage of chain extension. I is added to the mixture the way that the ratio of equivalents of non-reacted NCO:equivalents OH of I is about 8:1, or, preferably about 5:1, or more preferably from about 2:1. Reaction is continued at the same temperature as the first reaction of a prepolymer formation. Typical reaction time at 65° C. with a concentration of catalyst 100 ppm is from about 5 to about 6 hours. Upon completion of a reaction indicated by termination of disappearance of NCO characteristic absorption in the IR spectrum, a capping agent—hydroxyl substituted acrylate or methacrylate is added to the mixture which has residual non-reacted NCO. Upon completion of a capping reaction indicated by complete disappearance of NCO characteristic absorption in the IR spectrum the final urethane (meth)acrylate is formed. Typical reaction time at 65° C. with a concentration of catalyst 100 ppm is from about 8 to about 10 hours. A concentration of a capping agent is selected the way that a number of OH-equivalents of the capping agent is equal to a number of residual non-reacted NCO.

Another embodiment of the invention is a polymerizable composition comprising the above polymerizable urethane acrylate oligomer or urethane methacrylate oligomer and a polymerization initiator. Useful polymerization initiators non-exclusively include at least one of a peroxide, an azo compound, an organic, free radical polymerizable monomer, oligomer or polymer having at least one olefinically unsaturated double bonds. Examples of useful polymerization initiator comprises at least one of benzoyl peroxide, cumyl peroxide, 2,2'-azobis(2-methylpropionitryl) (AIBN), tert-butyl hydroperoxide, diethyl ether peroxide, bis(tert-butylcyclohexyl)peroxydicarbonate, cumyl hydroperxide and aliphatic hydroperoxides.

Other polymerization initiators comprise the least one free radical polymerizable component which is present in an amount sufficient to polymerize the urethane acrylate or methacrylate oligomer upon exposure to sufficient actinic radiation. Suitable polymerization initiators comprises a free radical polymerization initiator component which preferably photolytically generates free radicals. Examples of free radical generating components include photoinitiators which themselves photolytically generate free radicals by a fragmentation. Suitable initiators include aromatic ketones. Preferred examples thereof include benzophenone, benzoin, acetoin, acyloin, diketone, xanthone, thioxanthone, and ketocoumarin derivatives. Specific examples include benzophenone (CAS 119-61-9); Michler's ketone (CAS 90-94-1); benzoin methyl ether (CAS 3524-62-7); benzoin ethyl ether (CAS 574-09-4); 2-hydroxy-2-methylpropiophenone (CAS 7473-98-5); 1-hydroxycyclohexyl phenyl ketone (CAS 947-19-3); 2,2-diethoxyacetophenone (CAS 6175-45-7); camphorquinone (CAS 10373-78-1); 2-ethylanthraquinone (CAS 84-51-5); 2-tert-butylanthraquinone (CAS 84-47-9; 2,3-dichloro-1,4-naphthoquinone (CAS 117-80-6) 2-hydroxy-4'-(2-hydroxyethoxy)-2-methylpropiophenone (CAS 106797-53-9); methyl benzoylformate (CAS 15206-55-0); 2,2-dimethoxy-2-phenylacetophenone (CAS 24650-42-8); 2-ethylhexy-4-(dimethylamino)benzoate (CAS 21245-02-3); 2-ethyl-4-(dimethylamino)benzoate (CAS 10287-53-3); 2-isopropylthioxanthone (CAS 5495-84-1); 4-phenylbenzophenone (CAS 2128-93-0); and 2-benzyl-2-(dimethylamino)-4'-morpholinobutyrophenone (CAS 119313-12-1). In addition, suitable photoinitiators include phosphine oxides, such as diphenyl(2,4,6-trimethylbenzoyl)phosphine oxide (CAS 75980-60-8); and phenylbis(2,4,6-trimethylbenzoyl)phosphine oxide (CAS 162881-26-7).

The free radical generating component is preferably present in an amount sufficient to effect polymerization of the urethane acrylate or methacrylate oligomer compound upon exposure to sufficient actinic radiation, especially in the visible and/or ultraviolet region of the electromagnetic spectrum. The polymerization initiator may comprise from about 0.1 wt. % to about 50 wt. % of the non-solvent parts of the overall polymerizable composition, more preferably from about 0.1 wt. % to about 10 wt. %.

The overall polymerizable composition of the invention finds use as an adhesive or a coating composition. Although the radiation curable composition may comprise a compatible solvent, preferably the composition is substantially free of solvents, such as organic, nonreactive solvents.

The polymerizable composition may be prepared by admixing the composition components until a substantially homogenous fluid is formed. In one use, the polymerizable composition is formed and then exposed to sufficient actinic radiation to initiate the polymerization of the polymerizable urethane acrylate or methacrylate component. In another embodiment, the polymerizable composition is applied as a coating onto a surface and then exposed to sufficient actinic radiation to initiate the polymerization of the urethane acrylate or methacrylate component. In another embodiment, the polymerizable composition in the form of an adhesive is applied to a first surface and then contacting a second surface to the radiation curable composition, and then exposing the radiation curable adhesive composition to sufficient actinic radiation to initiate the polymerization of said polymerizable component while maintaining contact of the radiation curable adhesive composition with the first surface and the second surface. The polymerization of the polymerizable component may be initiated by exposure to visible and/or ultraviolet. In one embodiment, the polymerization of said polymerizable component may be initiated by exposure to radiation having a wavelength of from about 300 nm to about 465 nm, preferably about 360 nm to about 410 nm. In another embodiment, the polymerization of the polymerizable component may be initiated by exposure to ultraviolet radiation, visible radiation, or combinations thereof, by means of a light emitting diode such as those having an emission wavelength of from about 360 nm to about 465 nm, preferably about 380 nm to about 410 nm.

The length of time for exposure is easily determined by those skilled in the art and depends on the selection of the particular components of the radiation curable composition. Typically exposure ranges from about 1 second to about 60 seconds, preferably from about 2 seconds to about 30 seconds, and more preferably from about 2 seconds to about 15 seconds. Typical exposure intensities range from about 5 mW/cm$^2$ to about 600 W/cm$^2$, preferably from about 10 mW/cm$^2$ to about 450 W/cm$^2$, and more preferably from about 50 mW/cm$^2$ to about 300 W/cm$^2$.

Polymerizable composition which are Adhesive compositions according to the present invention may also contain other common adjuvants and additives, such as plasticizers, reactive and/or non-reactive diluents, flow auxiliaries, wetting agents, tackifiers, flame retardants, thixotropic and/or rheology control agents, ageing and/or corrosion inhibitors, stabilizers and/or coloring pigments. Depending on the requirements made of the adhesive application with respect to its processing properties, its flexibility, the required rigidifying action and the adhesive bond to the substrates, the relative proportions of the individual components may vary within comparatively wide limits which are easily determinable by those skilled in the art.

The following non-limiting examples serve to illustrate the invention.

Example 1

Stage 1

Hydroxythiol Modification

An amount of methoxypolyethyleneglycol monoacrylate (with 12 ethylene glycol repeating units) was added to a reaction vessel together with small amounts of methyldiethanolamine, as catalyst, and hydroquinone methyl ether, As an inhibitor of free-radical polymerization. Stirring was started and the batch warmed to 40° C. 2-Thioglycerol was added incrementally to control exothermic activity. The equivalent ratio of methoxypolyethyleneglycol monoacrylate and thioglycerol was 1:1. After exothermic activity ceased the batch was warmed to 65° C. and cooked for 2 hours. The reaction yielded >98% yield as determined by GPC with no free thioglycerol. This was confirmed by FTIR with no —SH being detected. The —OH equivalent weight of the product was calculated by dividing the total weight of the batch by the number of thioglycerol equivalents added.

The Stage 1 reaction scheme is given below.

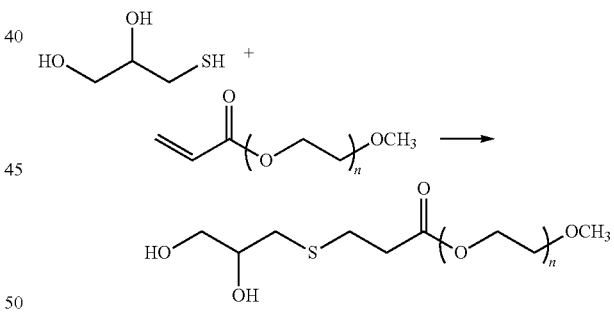

Stage 2

Urethane Acrylate Synthesis

An amount of isophorone diisocyanate was added to a reaction vessel at room temperature. Heating jacket temperature was adjusted to 45° C. suspended in a room temperature water bath and stirred. When the reaction batch temperature was 45° C., dibutyltin dilaurate (DBTDL), as catalyst, and 4-methoxy phenol (MEHQ), as free-radical polymerization inhibitor, were also added. Pentaerytritol triacrylate was added incrementally to control exothermic activity. When the exothermic activity ceased, the result of Stage I was added and batch temperature was adjusted to 60° C. The batch was kept at 60° C. until no free isocyanate was detected by FTIR.

Reaction scheme is given below. Viscosity of the product was 13,000 cP at 25° C. and it readily mixes with water. When the product was diluted with equal amount (by weight) of water viscosity was 50 cP at 25° C.

Example 2

Stage 1

Hydroxythiol Modification

An amount of methoxypolyethyleneglycol monoacrylate (with 23 ethylene glycol repeating units) was added to a reaction vessel together with small amounts of methyldiethanolamine, as catalyst, and hydroquinone methyl ether, as an inhibitor of free-radical polymerization. Stirring was started and the batch warmed to 40° C. 2-Thioglycerol was added incrementally to control exothermic activity. The equivalent ratio of methoxypolyethyleneglycol monoacrylate and thioglycerol was 1:1. After exothermic activity ceased the batch was warmed to 65° C. and cooked for 2 hours. The reaction yielded >98% yield as determined by GPC with no free thioglycerol. This was confirmed by FTIR with no —SH being detected. The —OH equivalent weight of the product was calculated by dividing the total weight of the batch by the number of thioglycerol equivalents added.

Stage 2

Urethane Acrylate Synthesis

An amount of dicyclohexylmethane-4,4'-diisocyanate (H$_{12}$MDI) was added to a reaction vessel at room temperature. Heating jacket temperature was adjusted to 45° C. suspended in a room temperature water bath and stirred. When the reaction batch temperature was 45° C., dibutyltindilaurate, as catalyst, and hydroquinone methyl ether, as free-radical polymerization inhibitor, were also added. Pentaerytritol triacrylate was added incrementally to control exothermic activity. When the exothermic activity ceased the result of Stage 1 was added and batch temperature was adjusted to 60° C. The batch was kept at 60° C. until no free isocyanate was detected by FTIR. Viscosity of the result was 11,750 cP at 25° C. and it readily mixes with water. When the result was diluted with equal amount (by weight) of water viscosity was 150 cP at 25° C.

Example 3

Stage 1

Hydroxythiol Modification

An amount of phenylthioethylacrylate (PTEA) was added to a reaction vessel together with small amounts of methyldiethanolamine, as catalyst, and hydroquinone methyl ether, as an inhibitor of free-radical polymerization. Stirring was started and the batch warmed to 40° C. 1-Thioglycerol was added incrementally to control exothermic activity. The equivalent ratio of PTEA$_{acrylate}$:Thioglycerol$_{SH}$ was 1:1. After exothermic activity ceased the batch was warmed to 65° C. and cooked for 2 hours. The reaction yielded >98% yield as determined by GPC with no free thioglycerol. This was confirmed by FTIR with no —SH being detected. The —OH equivalent weight of the product was calculated by dividing the total weight of the batch by the number of thioglycerol$_{OH}$ equivalents added.

The Stage 1 reaction scheme is given below.

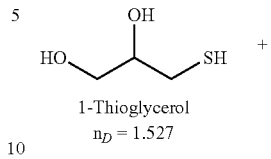

1-Thioglycerol
n$_D$ = 1.527

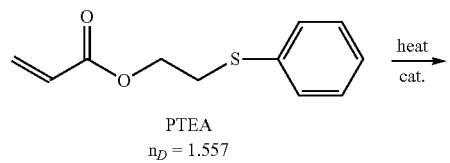

PTEA
n$_D$ = 1.557

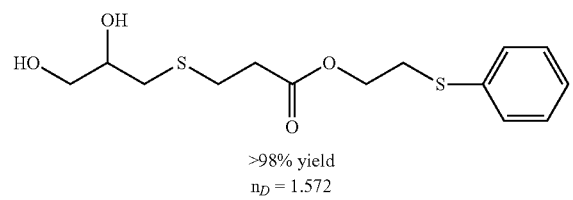

>98% yield
n$_D$ = 1.572

Stage 2

Urethane Acrylate Synthesis

An amount of toluene diisocyanate was added to a reaction vessel suspended in a room temperature water bath and stirred. The above product from Stage 1 was added incrementally to control exothermic activity. When the exothermic activity ceased the batch was heated to 82° C. and cooked for 1 hour. After the one hour cook the batch was cooled to 70° C. and polycaprolactone acrylate was added followed by an addition of hydroxyethylacrylate (HEA). A small amount of dibutyltindilaurate, a urethane catalyst, was also added to aid bringing the reaction to completion. The batch was cooked at 82° C. until no free isocyanate was detected by FTIR. The equivalent ratio of TDI:Stage 1 product:polycaprolactone acrylate:HEA was 2.0:1.0:0.5:0.5.

The theoretical structure of the urethane acrylate product is given below. Its n$_D$ was measured at 1.555.

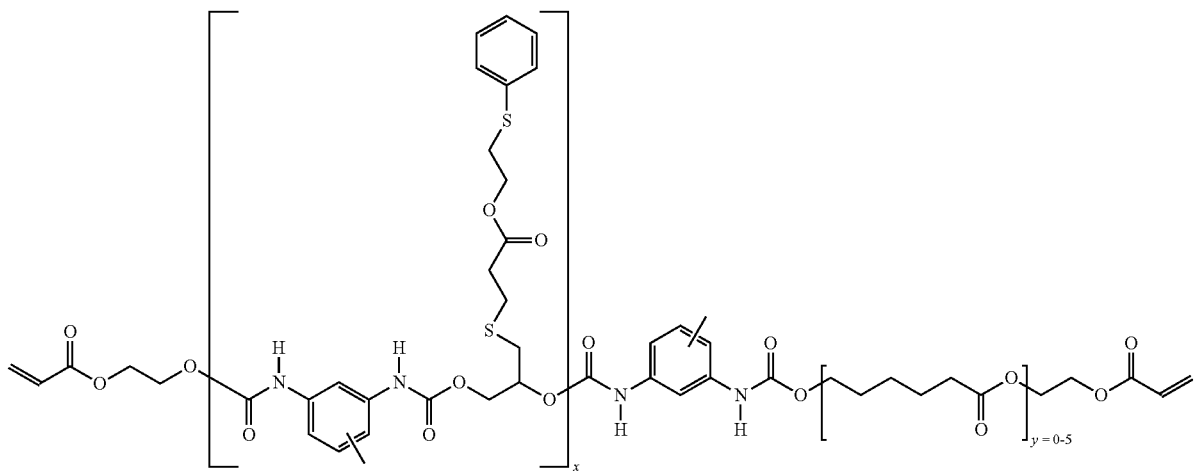

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A polymerizable composition which comprises a urethane acrylate oligomer or urethane methacrylate oligomer of the formula:

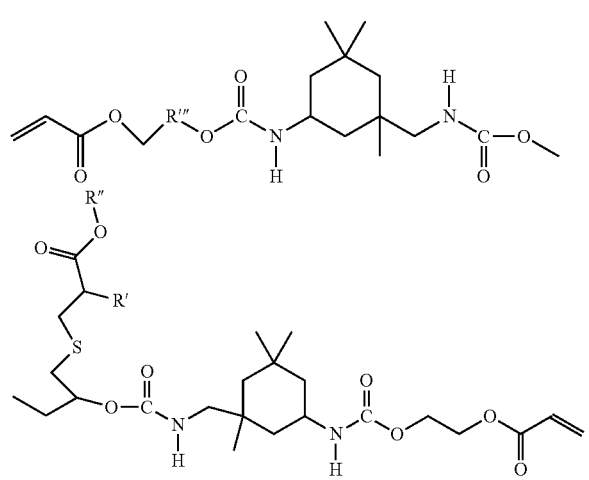

wherein n is 1 to 50
R'=—H, —CH$_3$;
R''=is a linear or branched C$_1$ to C$_{30}$ alkyl group, a linear or branched C$_3$ to C$_{30}$ alkenyl group, a C$_6$ to C$_{22}$ aryl group, a polyethylene glycol containing group, a (poly)ethylene glycol mono methyl ether containing group, a (poly)ethylene glycol mono ethyl ether containing group, a lauryl group, a silicone containing group, an alkoxysilane containing group, Si(OCH$_3$)$_3$ containing group, a fluorinated alkyl group, a brominated alkyl group, or a benzene derivative,

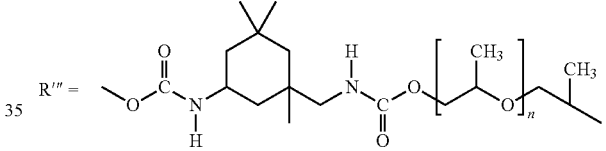

2. A polymerizable composition comprising the polymerizable urethane acrylate oligomer or urethane methacrylate oligomer of claim 1, and a polymerization initiator.

3. The polymerizable composition of claim 2 wherein the polymerization initiator comprises at least one of a peroxide, an azo compound, and a free radical generating photoinitiator.

4. The polymerizable composition of claim 2 wherein the polymerization initiator comprises at least one of benzoyl peroxide, cumyl peroxide, 2,2'-azobis(2-methylpropionitryl) (AIBN), tert-butyl hydroperoxide, diethyl ether peroxide, bis (tert-butylcyclohexyl)peroxydicarbonate, cumyl hydroperxide and aliphatic hydroperoxides.

5. The polymerizable composition of claim 2 wherein the polymerization initiator comprises the least one free radical generating photoinitiator which is present in an amount sufficient to polymerize the urethane acrylate or methacrylate oligomer upon exposure to sufficient actinic radiation.

* * * * *